United States Patent [19]
Levinson

[11] Patent Number: 5,828,725
[45] Date of Patent: Oct. 27, 1998

[54] PROCESSING IMAGES FOR REMOVAL OF ARTIFACTS

[75] Inventor: Reuven Levinson, Haifa, Israel

[73] Assignee: Eliav Medical Imaging Systems LTD, Haifa, Israel

[21] Appl. No.: 880,529

[22] Filed: Jun. 23, 1997

[30] Foreign Application Priority Data

Jul. 3, 1996 [IL] Israel ........................................ 118784

[51] Int. Cl.$^6$ ................................................ H65G 1/64
[52] U.S. Cl. ............................................. 378/98; 382/275
[58] Field of Search .............................. 378/62, 98, 901; 382/132, 275

[56] References Cited

U.S. PATENT DOCUMENTS

| | | | |
|---|---|---|---|
| 5,231,574 | 7/1993 | Agano | 382/132 |
| 5,671,264 | 9/1997 | Florent et al. | 378/98 |

*Primary Examiner*—David P. Porta
*Assistant Examiner*—David Vernon Bruce
*Attorney, Agent, or Firm*—Benjamin J. Barish

[57] ABSTRACT

A method and apparatus for processing images received on an image sensor of rectangular configuration bounded by four outer edges and including a plurality of pixel elements arranged in a rectangular matrix includes the following operations: A. locating an initial rectangular-matrix region consisting of pixel elements determined to be free of an artifact; B. sequentially testing each pixel element along two contiguous outer edges of the image sensor, starting from the initial rectangular-matrix region, to determine whether the pixel value of the tested pixel element is sufficiently large to indicate the probability of an artifact, and for each such pixel element found to have such a pixel value, replacing its pixel value with another having a relation to the pixel value of its closest neighbours found to be free of an artifact, thereby cleaning the respective pixel element; and C. cleaning in a similar manner each of the remaining pixel elements.

20 Claims, 5 Drawing Sheets

FIG. 3

|   | $C_1$ |   |   |   | $C_5$ |   |   | ... |   | $C_N$ |
|---|---|---|---|---|---|---|---|---|---|---|
|   | (1,1) | (1,2) | (1,3) | (1,4) | (1,5) |   |   |   |   |   |
|   | (2,1) | (2,2) | (2,3) | (2,4) | (2,5) | (2,6) | (2,7) | ... | (2,M-2) | (2,M-1) |
|   | (3,1) | (3,2) | (3,3) | (3,4) | (3,5) | (3,6) | (3,7) | ... | (3,M-2) | (3,M-1) |
|   | (4,1) | (4,2) | (4,3) | (4,4) | (4,5) | (4,6) | (4,7) | ... | (4,M-2) | (4,M-1) |
| $R_5$ | (5,1) | (5,2) | (5,3) | (5,4) | (5,5) | (5,6) | (5,7) | ... | (5,M-2) | (5,M-1) |
|   |   | (6,2) | (6,3) | (6,4) | (6,5) | (6,6) | (6,7) | ... | (6,M-2) | (6,M-1) |
|   |   | (7,2) | (7,3) | (7,4) | (7,5) | (7,6) | (7,7) | ... | (7,M-2) | (7,M-1) |
|   |   | ... | ... | ... | ... | ... | ... |   |   |   |
|   |   | (N-2,2) | (N-2,3) | (N-2,4) | (N-2,5) | (N-2,6) | (N-2,7) |   | (N-2,M-2) | (N-2,M-1) |
| $R_M$ |   | (N-1,2) | (N-1,3) | (N-1,4) | (N-1,5) | (N-1,6) | (N-1,7) |   | (N-1,M-2) | (N-1,M-1) |

FIG. 4

| (P-1,Q-1) | (P-1,Q) | (P-1,Q+1) |
|---|---|---|
| (P,Q-1) | (P,Q) | (P,Q+1) |
| (P+1,Q-1) | (P+1,Q) | (P+1,Q+1) |

PROCESSING IMAGES FOR REMOVAL OF ARTIFACTS

FIELD AND BACKGROUND OF THE INVENTION

The present invention relates to a method and apparatus for processing images in order to remove artifacts. The invention is particularly useful for removing artifacts from images generated by CCD cameras in X-ray imaging applications, and is therefore described below with respect to this application.

X-ray imaging is used in both industrial and medical settings. Many imaging applications involve real-time image display. Typically, in real-time imaging applications the X-ray beam is converted to a light beam by a scintillating plate. The light beam is incident on a CCD camera which converts the light beam to an electrical video signal, and the image is then displayed in real-time on a video monitor.

In addition to light, CCD cameras are also sensitive to X-ray radiation. In X-ray imaging, scattered X-ray radiation is produced in the object being examined and is emitted from the object in multiple directions, different from the direction of the primary X-ray beam. If the scattered radiation is incident on a CCD camera, it produces artifacts in the displayed image.

In order to reduce the influence of the scattered radiation, the CCD camera may be placed inside a lead shield and/or distanced from the object being examined. Both procedures result in additional mechanical complexity to the imaging system; and in the case of distancing the camera from the object, there may also be reduction in the image quality.

There is therefore a need for a method and apparatus to eliminate image artifacts from image sensors, particularly artifacts resulting from the scattered X-ray radiation, without increasing the mechanical complexity of the system or reducing the system's image quality.

BRIEF SUMMARY OF THE INVENTION

According to the present invention, there is provided a method of processing images received on an image sensor of rectangular configuration bounded by four outer edges and including a plurality of pixel elements arranged in a rectangular matrix of horizontal rows and vertical columns, comprising the following operations:

A. locating an initial rectangular-matrix region consisting of pixel elements determined to be free of an artifact;

B. sequentially testing each pixel element along two contiguous outer edges of the image sensor, starting from the initial rectangular-matrix region, to determine whether the pixel value of the tested pixel element is sufficiently large to indicate the probability of an artifact, and for each such pixel element found to have such a pixel value, replacing its pixel value with another having a relation to the pixel value of its closest neighbours found to be free of an artifact, thereby cleaning the respective pixel element; and C. testing each of the remaining pixel elements to determine whether its pixel value is sufficiently large to indicate the probability of an artifact, and for each such pixel element found to have such a pixel value, replacing its pixel value with another pixel value having a predetermined relationship to the pixel values of its closest neighbours, thereby cleaning the respective pixel elements.

According to further features in the described preferred embodiment, Operation A is performed by:

(a) calculating the standard deviation of the pixel values in a selected initial rectangular-matrix region of the image sensor;

(b) determining whether the calculated standard deviation exceeds a predetermined threshold;

(c) if not, determining the initial rectangular-matrix region to be free of an artifact; and (d) if the calculated standard deviation is determined to exceed the threshold, incrementing the selected initial rectangular-matrix region by one pixel element, and repeating (a), (b) and (c) until an initial rectangular-matrix region is determined to be free of an artifact.

The threshold value in this operation, as well as in the operations described below, depends on a number of factors, including the noise level of the image, the spatial frequency of the object being examined, and the MTF of the imaging system. The threshold value in each case is determined by examining a typical image and determining the minimum change in pixel value that would result in a white dot indicating an artifact. This determination is generally made visually beforehand. For example, for radiotherapy portal images acquired with a 1 cGy exposure, a threshold value of 10 is used for 256-unit (8-bit) images.

According to further features in the described preferred embodiment, Operation B includes the steps:

(a) determining whether the pixel value of each tested pixel element bears a predetermined relationship with respect to clean neighbouring pixel elements, and (b) if not, replacing the pixel value of the tested pixel element by a pixel value having another predetermined relationship with respect to its clean neighbouring pixel elements.

In the described preferred embodiment, the predetermined relationship of step (a) is whether the pixel value of the tested pixel element is equal to or less than the pixel value of any one of a number of clean neighbouring pixel elements plus a predetermined threshold, and the predetermined relationship of step (b) is the average of the number of clean neighbouring pixel elements. In the described embodiment, "in" is 2.

According to further features in the described preferred embodiment, Operation C includes:

(a) determining, in a first step, whether the pixel value of each tested pixel element bears a first predetermined relationship to the four clean neighbouring pixel elements; and if not (b) determining, in a second test more detailed than the first test, whether the pixel value of the tested pixel element bears a second relationship to all eight of the neighbouring pixel elements; and if not (c) replacing the pixel value of the tested pixel element with the average of the pixel values of at least some of the eight neighbouring pixel elements involved in the second test.

The invention also provides apparatus for processing images in accordance with the above method.

It will thus be seen that the invention enables image artifacts to be removed by a technique which does not reduce the image quality of the images or introduce any other image artifacts, and which can be implemented efficiently and quickly on a digital computer.

Further features and advantages of the invention will be apparent from the description below.

BRIEF DESCRIPTION OF THE DRAWINGS

The invention is herein described, by way of example only, with reference to the accompanying drawings, wherein:

FIG. 3 illustrates a typical array of pixel elements in a CCD image sensor which will be referred to in describing how the image sensor is cleaned of artifacts;

FIG. 4 illustrates the neighbours of a tested pixel element (P, Q);

DESCRIPTION OF A PREFERRED EMBODIMENT

Overall System

Figure 1:
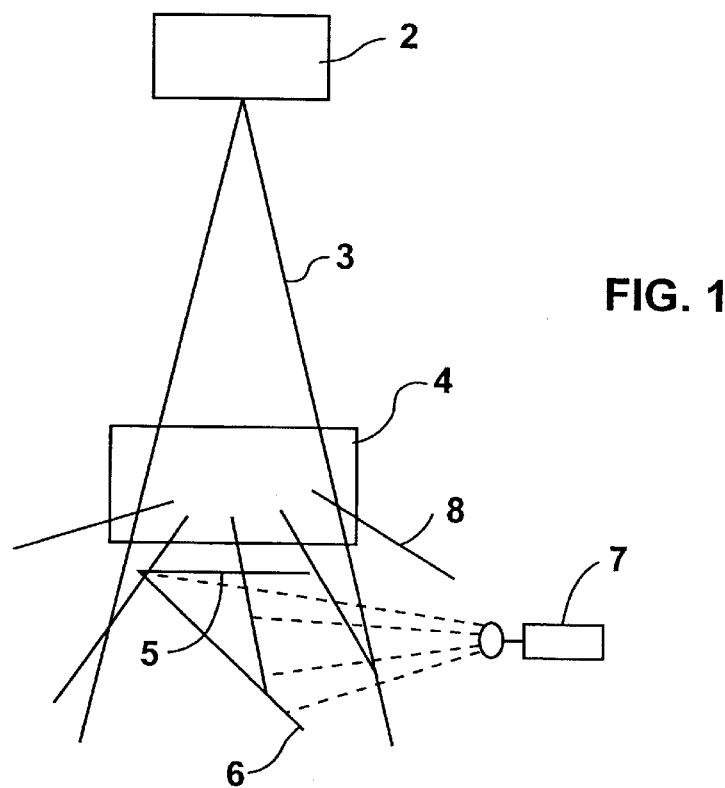
FIG. 1 schematically illustrates a CCD-based X-ray imaging system.

The X-ray imaging system illustrated in FIG. 1 includes an X-ray tube 2 which directs an X-ray beam 3 to the object 4 under examination, e.g., a person, an industrial device, etc. The X-rays transmitted through the object 4 are detected by an X-ray detector 5 having a scintillating plate which converts the detected X-rays to light. Such light is reflected by a mirror 6 to a CCD camera or other image sensor 7.

As mentioned earlier, the CCD camera 7 is also sensitive to X-ray radiation, and particularly to the scattered X-ray radiation produced in the object being examined. Such scattered radiation is emitted from the object in multiple directions, as shown at 8 in FIG. 1. Therefore any such scattered radiation reaching the CCD camera 7 will produce artifacts in the displayed image.

Figure 2:
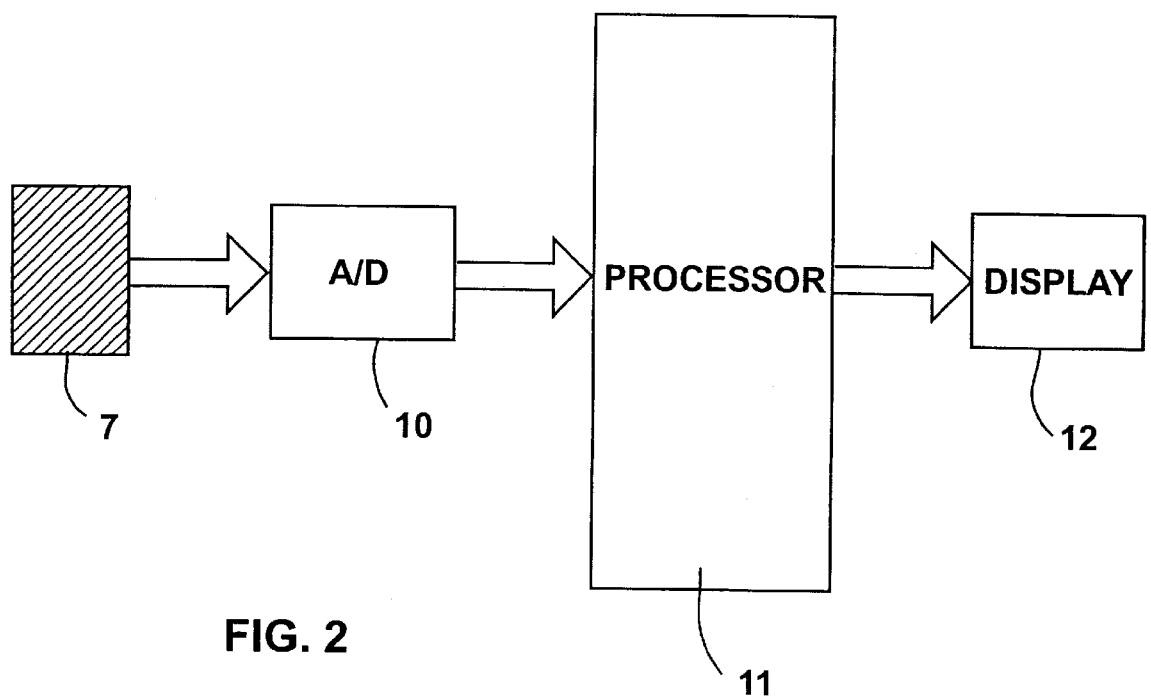
FIG. 2 is a block diagram illustrating the main electrical components of the system of FIG. 1.

FIG. 2 illustrates the main components of the electrical system for processing the output of the CCD camera 7 in order to remove such artifacts. Thus, as shown in FIG. 2, the output of the CCD camera 7 is converted to digital form by an A/D converter 10 and is then fed to a processor 11 which processes such digital signals according to the techniques described below in order to remove the artifacts from the image before the image is displayed in the display monitor 12 or otherwise processed.

The procedure in processor 11 examines each pixel of the image. The pixel's gray value is compared to the gray value of its immediate neighbours. If the pixel's gray value is higher than a threshold value, the pixel is identified as an artifact pixel and its gray value is replaced by a corrected gray value, which is the average gray value of its neighbouring pixels.

Because of the nature of the influence of the X-rays on the CCD camera, the artifact pixel will always have a higher gray level value than its "true" value. The procedure described below will only identify artifact pixels as those with pixel gray values greater than a calculated threshold value from the average gray value of neighbouring pixels.

The image artifacts appear as both singular white pixel or alternatively as clusters of white pixels. The singular and clustered appearance are both functions of nature of the "X-ray CCD chip" interaction. The X-rays interact with the CCD chip and recoil electrons are produced which deposit energy in the chip and create the image artifact in the form of a white dot.

Because of the high energy of the recoil electrons they can exit the origin pixel (in which they were created) and enter neighbouring pixels; deposit energy in the neighbouring pixels, and create additional white dots. In this case, the result is a cluster of two or more white dots. In addition, the recoil electrons create delta rays which are emitted in multiple directions with respect to the direction of the recoil electron. The delta rays can also traverse pixel borders and create additional white dots and clusters of white dots.

The procedure described below identifies both singular white dots and clusters of white dots. In the case of clusters of white dots, neighbouring pixels are themselves image artifacts, and must not be used to calculate the corrected pixel gray values. In the calculation of the corrected pixel gray values the procedure uses only neighbouring pixels that have already been corrected or otherwise determined to be true artifact-free pixels.

Figure 5:
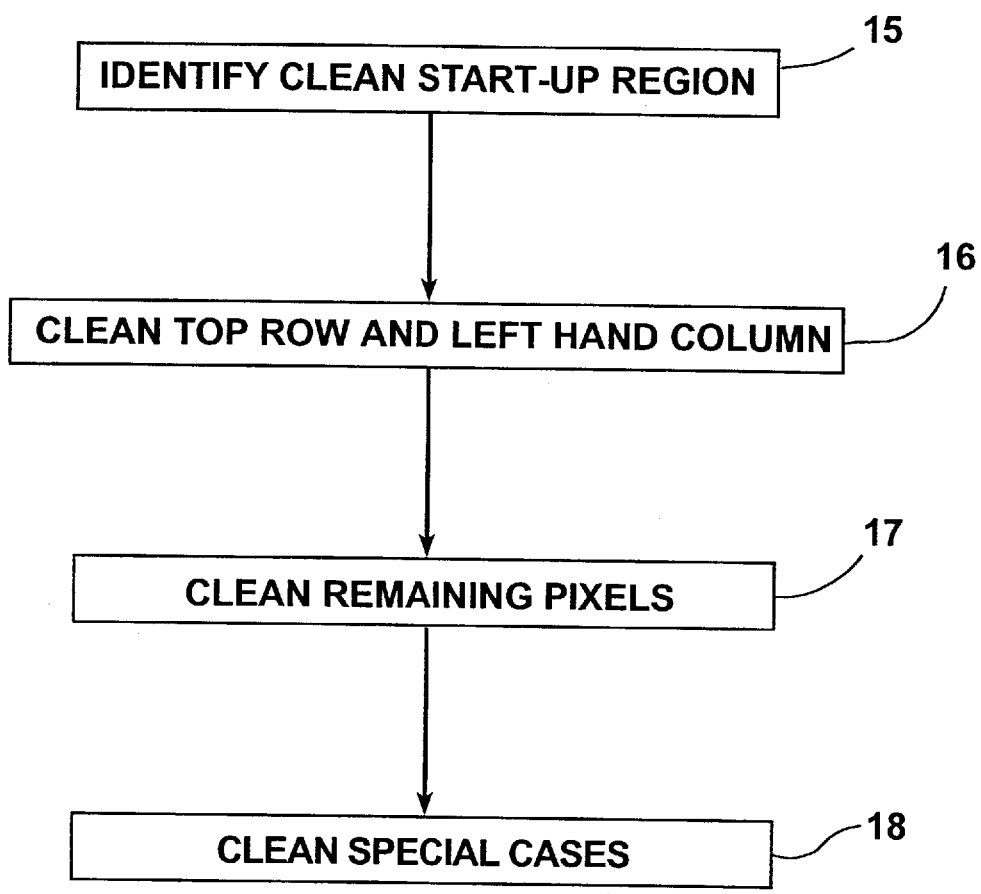
FIG. 5 is a general flow chart illustrating one manner of removing artifacts from an image in accordance with the present invention.

Briefly, this procedure involves the following main operations as shown in the general flow chart of FIG. 5:

A. identifying a clean start-up region (box 15), by locating an initial rectangular-matrix region consisting of pixel elements determined to be free of an artifact;

B. cleaning the top row and left-hand column (box 16), by sequentially testing each pixel element along these two contiguous outer edges of the image sensor, starting from the initial rectangular-matrix region, to determine whether the pixel value of the tested pixel element is sufficiently large to indicate the probability of an artifact, and for each such pixel element found to have such a pixel value, replacing its pixel value with another having a relation to the pixel value of its closest neighbours found to be free of an artifact, thereby cleaning the respective pixel element; and C. cleaning the remaining pixels (box 17), and special case pixels (box 18). In this operation, each of the remaining pixel elements is tested to determine whether its pixel value is sufficiently large to indicate the probability of an artifact, and for each such pixel element found to have such a pixel value, its pixel value is replaced with another pixel value having a predetermined relationship to the pixel values of its closest neighbours, thereby also cleaning the tested pixel elements. The foregoing procedure is followed for all the remaining pixels (indicated by box 17), whereas a modified procedure is followed with respect to the pixels in the rightmost column and lowest row, since these pixels do not have as many neighbours as the others, and therefore these are considered "special cases" (box 18).

FIG. 3 illustrates a typical image sensor including a rectangular matrix of pixel elements arranged in a plurality of vertical columns $C_1$–$C_n$, and a plurality of horizontal rows $R_1$–$R_m$. It wil thus be seen that the rectangular image sensor of FIG. 3 is bounded on its four outer edges by the pixel elements of column $C_1$, row $R_1$, column $C_n$, and row $R_m$.

Operation A (Box 15, FIG. 5)

Operation A involves locating an initial rectangular matrix region consisting of pixel elements determined to be free of an artifact. In the example illustrated in FIG. 3, this initial region is a 5×5 matrix of the pixel elements in the upper-left corner of the image sensor 7, constituted of the pixel elements in columns $C_1$–$C_5$ and in rows $R_1$–$R_5$.

In Operation A, processor 11 performs a special start-up routine in which it:

(a) calculates the standard deviation (SD) of the pixel values in the initial rectangular matrix region, and (b) determines whether the calculated standard deviation exceeds a predetermined threshold.

If it does not, it can be concluded that all the pixels in the region are artifact free. However, if the standard deviation is determined to exceed the predetermined threshold, processor 11 increments the initial region by one pixel, in either of the two directions, and repeats the foregoing steps until an initial region is located found to be artifact free in accordance with the above steps.

As shown, the standard deviation (SD) is determined as follows:

$$SD = \sqrt{\Sigma (Pi - P)^2}$$

where: Pi is the value of each pixel

P is the average value of the 5×5 matrix

The foregoing procedure is very calculation intensive, and therefore is only done for the small initial start-up region. As shown in FIG. 3, this initial region is preferably at a corner, particularly the upper-left corner, of the image sensor.

The threshold used in this operation is selected beforehand based on the inherent noise characteristics of the image as briefly described above. A single white dot in the region would make the standard deviation of the entire region greater than the threshold.

Figure 6A:
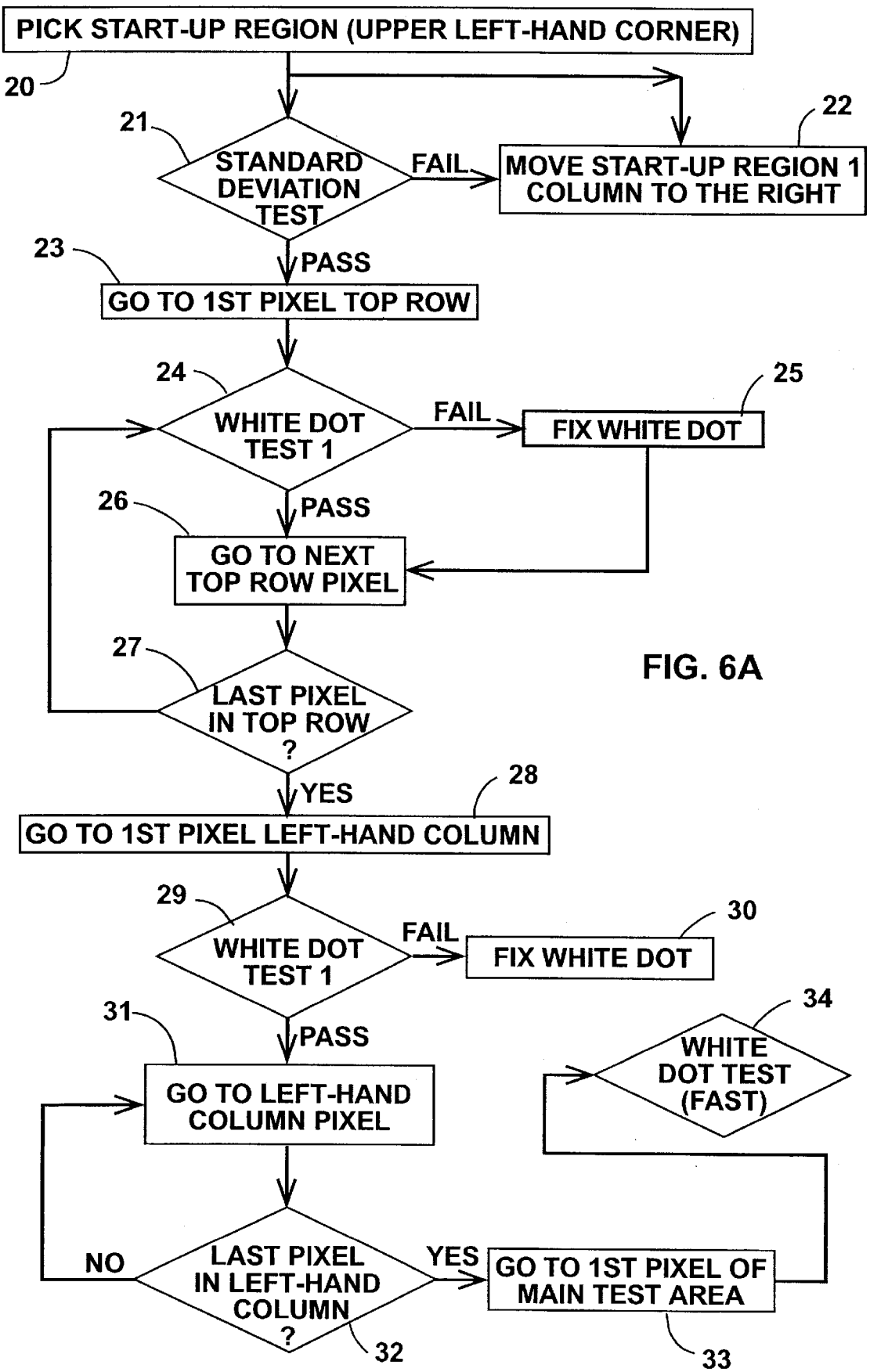
FIGS. 6a and 6b, taken together, constitute a more detailed flow chart illustrating one manner of removing artifacts from an image in accordance with the present invention.

The foregoing steps are illustrated by boxes 20, 21 and 22 in the detailed flow chart of FIG. 6*a*.

Operation B (Box 16, FIG. 5)

Assuming that the matrix in the upper-left corner of the image is determined to be clean, the top row $R_1$ of pixel elements is then tested and cleaned, and similarly the first column $C_1$ of pixel elements is tested and cleaned. This is done by testing each pixel in sequence and comparing its value with the two preceding neighbours in the respective row or column (which neighbours have been found to be clean), and determine whether each tested pixel element bears a predetermined relationship with respect to these clean neighbours. If not, the tested pixel element is replaced by a pixel value having a predetermined relationship with respect to its clean neighbour pixel elements.

Preferably, this predetermined relationship is whether the pixel value of the tested pixel element is equal to or less than the pixel value of either one of the two closest clean pixel elements in the respective row or column plus a predetermined threshold based on the inherent noise characteristics of the image. Since the two preceding neighbours are both clean, it will be seen that if a tested pixel element passes this test it must also be clean. If, however, the value of the tested pixel element is found to be greater than both of the preceding clean pixels plus the predetermined threshold, this indicates the presence of an artifact (white dot). In such case, the value of the tested pixel element is replaced by the average of the two clean adjacent pixel elements.

The top row $R_1$ of pixel elements is thus cleaned in this manner, whereupon the first column $C_1$ of pixel elements is then cleaned in this manner.

Boxes 23–32 in the flow chart of FIG. 6*a* illustrates this operation.

Operation C (Boxes 17, 18, FIG. 5)

After the top row ($R_1$) and left column ($C_1$) of pixel elements have been tested and cleaned as described above under Operation B, the remaining pixels are cleaned under this Operation C. This is done in two steps for each pixel element as follows:

(a) determining, in a first step, whether the pixel value of each tested pixel element bears a first predetermined relationship to the four clean neighbouring pixel elements, and if not;

(b) determining, in a second test more detailed than the first test, whether the pixel value of the tested pixel element bears a second relationship to all eight of the neighbouring pixel elements. If the pixel element passes neither test, the pixel value of the tested pixel element is replaced by the average of the pixel values of at least some of the eight neighbouring pixel elements involved in the second test.

In the fast test of step (a) above, the predetermined relationship is whether the pixel value of the tested pixel element is equal to or less than the average of the four clean neighbouring pixel elements, plus a predetermined threshold. Thus, as shown in FIG. 4, each tested pixel (P, Q) has eight neighbours, four of which have been previously cleaned, and the other four which have not yet been cleaned. For testing pixel element (P, Q) of FIG. 4, the value of the four clean pixel elements (namely the three neighbours in the top row of FIG. 4 and the pixel element immediately to the left of the tested pixel element) are averaged, and the value of the tested pixel element (P, Q) is checked to determine whether it is equal to or less than this average, plus a predetermined threshold. If the tested pixel element is found to pass this "fast test", indicated by blocks 33 and 34 in FIGS. 6*a*, 6*b*, the next pixel is tested (box 35). However, if the tested pixel element does not pass this "fast test", a "detailed test" is performed, as indicated by box 36 in FIG. 6*b*.

In the "detailed test", all eight of the neighbouring pixel elements are considered, and those having the four lowest values are averaged. A determination is then made whether the value of the tested pixel element is equal to or less than this average, plus a predetermined threshold (box 36, FIG. 6*b*). If a tested pixel element passes this test, the system then proceeds to the next pixel (box 35). However, if the tested pixel element does not pass this "detailed test", step (c) as set forth is performed wherein the value of the tested pixel is replaced by the average of the values in the four lowest-order neighbouring pixels. This step is indicated by box 37 in the flow chart of FIG. 6*b*.

The foregoing "fast test" and "detailed test" are performed for all the remaining pixels of the image sensor (indicated by box 17, FIG. 5), except for those in the last row $R_m$ and right-hand column $C_n$ since these pixel elements do not have eight neighbours, four of which are clean, but rather have only five neighbours, three of which are clean. Therefore, with respect to these "special case" pixel elements, a modified procedure is followed (indicated by box 18, FIG. 5) in which: the "fast test" of step (a) involves only three clean neighbouring pixel elements (instead of four); the "detailed test" of step (b) involves comparing five neighbouring pixels (instead of eight), and using the values of the three (instead of four) lowest-value pixel elements for comparison; and step (c) involves replacing a pixel element that failed both tests by the average value of the lowest three (instead of four) neighbouring pixel elements.

Figure 6B:
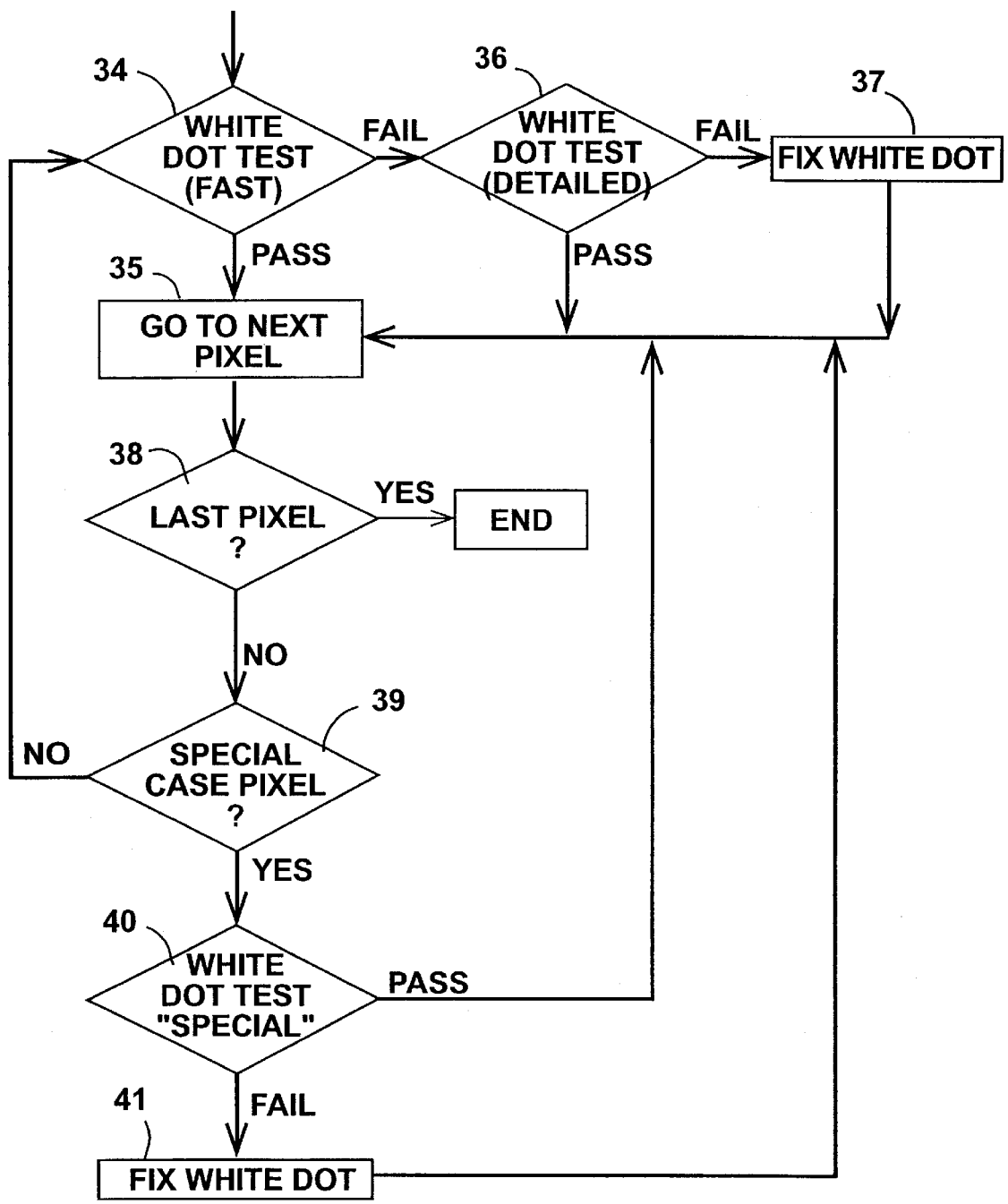

The foregoing operations are indicated by boxes 39, 40 and 41 in FIG. 6*b*.

As one example, a threshold of "3" can be used in Operation A, a threshold of "30" can be used in Operation B; and a threshold of "10" can be used for both the "fast test" and "detailed test" in Operation C.

While the invention has been described with respect to one preferred embodiment, it will be appreciated that this is set forth merely for purposes of example, and that many other variations, modifications and applications of the invention may be made.

I claim:

1. A method of processing images received on an image sensor of rectangular configuration bounded by four outer edges and including a plurality of pixel elements arranged in a rectangular matrix of horizontal rows and vertical columns, comprising the following operations:

A. locating an initial rectangular-matrix region consisting of pixel elements determined to be free of an artifact;

B. sequentially testing each pixel element along two contiguous outer edges of the image sensor, starting from said initial rectangular-matrix region, to determine whether the pixel value of the tested pixel element is sufficiently large to indicate the probability of an artifact, and for each such pixel element found to have such a pixel value, replacing its pixel value with another having a relation to the pixel value of its closest neighbours found to be free of an artifact, thereby cleaning the respective pixel element; and C. testing each of the remaining pixel elements to determine whether its pixel value is sufficiently large to indicate the probability of an artifact, and for each such pixel element found to have such a pixel value, replacing its pixel value with another pixel value having a predetermined relationship to the pixel values of its closest neighbours, thereby cleaning the respective pixel element.

2. The method according to claim 1, wherein Operation A is performed by:

(a) calculating the standard deviation of the pixel values in a selected initial rectangular-matrix region of the image sensor;

(b) determining whether said calculated standard deviation exceeds a predetermined threshold;

(c) if not, determining said initial rectangular-matrix region to be free of an artifact; and (d) if said calculated standard deviation is determined to exceed said threshold, incrementing the selected initial rectangular-matrix region by one pixel element, and repeating (a), (b) and (c) until an initial rectangular-matrix region is determined to be free of an artifact.

3. The method according to claim 2, wherein said selected initial rectangular-matrix region is at a corner of the image sensor.

4. The method according to claim 3, wherein said selected initial rectangular matrix region is at the left-hand corner of the image sensor.

5. The method according to claim 1, wherein said Operation B includes the steps:

(a) determining whether the pixel value of each tested pixel element bears a predetermined relationship with respect to clean neighbouring pixel elements, and (b) if not, replacing the pixel value of the tested pixel element by a pixel value having another predetermined relationship with respect to its clean neighbouring pixel elements.

6. The method according to claim 5, wherein said predetermined relationship of step (a) is whether the pixel value of the tested pixel element is equal to or less than the pixel value of any one of a number of clean neighbouring pixel elements plus a predetermined threshold, and the predetermined relationship of step (b) is the average of said number of clean neighbouring pixel elements.

7. The method according to claim 6, wherein said number of clean neighbouring pixel elements in both step (a) and step (b) is "2".

8. The method according to claim 1, wherein said Operation C includes:

(a) determining, in a first step, whether the pixel value of each tested pixel element bears a first predetermined relationship to the four clean neighbouring pixel elements; and if not (b) determining, in a second test more detailed than the first test, whether the pixel value of the tested pixel element bears a second relationship to all eight of the neighbouring pixel elements; and if not (c) replacing the pixel value of the tested pixel element with the average of the pixel values of at least some of said eight neighbouring pixel elements involved in said second test.

9. The method according to claim 8, wherein, in testing all said pixel elements in Operation C except for those in the remaining two contiguous outer edges of the image sensor, (a) said first test in step (a) is whether the pixel value of the tested pixel element is equal to or less than the average of the four clean neighbouring pixel elements plus a predetermined threshold;

(b) said second test in step (b) is whether the pixel value of the tested pixel elements is equal to or less than the average of the four lowest-value pixel elements of all eight neighbouring pixel elements plus a predetermined threshold;

(c) and in testing the pixel elements in Operation C in said remaining two contiguous outer edges of the image sensor, said first and second predetermined relations are as set forth in (a) and (b) above, except that the relationship in (a) involves three clean neighbouring pixel elements, and the relationship in (b) involves five neighbouring pixel elements.

10. The method according to claim 1, wherein said initial rectangular-matrix region is a matrix of 5×5 pixel elements.

11. Imaging apparatus comprising:

an image sensor of rectangular configuration bounded by four outer edges and including a plurality of pixel elements arranged in a rectangular matrix of horizontal rows and vertical columns;

and a data processor programmed to perform the following operations:

A. locating an initial rectangular-matrix region consisting of pixel elements determined to be free of an artifact;

B. sequentially testing each pixel element along two contiguous outer edges of the image sensor, starting from said initial rectangular-matrix region, to determine whether the pixel value of the tested pixel element is sufficiently large to indicate the probability of an artifact, and for each such pixel element found to have such a pixel value, replacing its pixel value with another having a relation to the pixel value of its closest neighbours found to be free of an artifact, thereby cleaning the respective pixel element; and C. testing each of the remaining pixel elements to determine whether its pixel value is sufficiently large to indicate the probability of an artifact, and for each such pixel element found to have such a pixel value, replacing its pixel value with another pixel value having a predetermined relationship to the pixel values of its closest neighbours, thereby cleaning the respective pixel element.

12. The apparatus according to claim 11, wherein said data processor is programmed to perform said Operation A by:

(a) calculating the standard deviation of the pixel values in a selected initial rectangular-matrix region of the image sensor;

(b) determining whether said calculated standard deviation exceeds a predetermined threshold;

(c) if not, determining said initial rectangular-matrix region to be free of an artifact; and (d) if said calculated standard deviation is determined to exceed said threshold, incrementing the selected initial rectangular-matrix region by one pixel element, and repeating (a), (b) and (c) until an initial rectangular-matrix region is determined to be free of an artifact.

13. The apparatus according to claim 12, wherein said selected initial rectangular-matrix region is at a corner of the image sensor.

14. The apparatus according to claim 13, wherein said selected initial rectangular matrix region is at the left-hand corner of the image sensor.

15. The apparatus according to claim 11, wherein said data processor is programmed to perform Operation B by:

(a) determining whether the pixel value of each tested pixel element bears a predetermined relationship with respect to clean neighbouring pixel elements, and (b) if not, replacing the pixel value of the tested pixel element by a pixel value having another predetermined relationship with respect to its clean neighbouring pixel elements.

16. The appartus according to claim 15, wherein said predetermined relationship of step (a) is whether the pixel value of the tested pixel element is equal to or less than the pixel value of any one of a number of clean neighbouring pixel elements plus a predetermined threshold, and the predetermined relationship of step (b) is the average of said number of clean neighbouring pixel elements.

17. The apparatus according to claim 16, wherein said number of clean neighbouring pixel elements in both step (a) and step (b) is "2".

18. The apparatus according to claim 11, wherein said data processor is programmed to perform said Operation C by:

(a) determining, in a first step, whether the pixel value of each tested pixel element bears a first predetermined relationship to the four clean neighbouring pixel elements; and if not (b) determining, in a second test more detailed than the first test, whether the pixel value of the tested pixel element bears a second relationship to all eight of the neighbouring pixel elements; and if not (c) replacing the pixel value of the tested pixel element with the average of the pixel values of at least some of said eight neighbouring pixel elements involved in said second test.

19. The apparatus according to claim 18, wherein, in testing all said pixel elements in Operation C except for those in the remaining two contiguous outer edges of the image sensor, (a) said first test in step (a) is whether the pixel value of the tested pixel element is equal to or less than the average of the four clean neighbouring pixel elements plus a predetermined threshold;

(b) said second test in step (b) is whether the pixel value of the tested pixel elements is equal to or less than the average of the four lowest-value pixel elements of all eight neighbouring pixel elements plus a predetermined threshold;

(c) and in testing the pixel elements in Operation C in said remaining two contiguous outer edges of the image sensor, said first and second predetermined relations are as set forth in (a) and (b) above, except that the relationship in (a) involves three clean neighbouring pixel elements, and the relationship in (b) involves five neighbouring pixel elements.

20. The apparatus according to claim 11, wherein said imaging apparatus is X-ray imaging apparatus.

* * * * *